(12) United States Patent
Schumann et al.

(10) Patent No.: US 7,540,168 B2
(45) Date of Patent: Jun. 2, 2009

(54) CRYOGENIC STORAGE CONTAINER SYSTEM

(75) Inventors: Cass Schumann, St. Clair Shores, MI (US); Edward Teper, Jr., Algonac, MI (US); Kevin Heintz, Marine City, MI (US); Scott Walker, Sterling Heights, MI (US); John Brothers, Clinton Township, MI (US)

(73) Assignee: Custom Biogenic Systems, Shelby Township, MI (US)

( * ) Notice: Subject to any disclaimer, the term of this patent is extended or adjusted under 35 U.S.C. 154(b) by 223 days.

(21) Appl. No.: 11/551,281

(22) Filed: Oct. 20, 2006

(65) Prior Publication Data

US 2008/0092581 A1 Apr. 24, 2008

(51) Int. Cl.
*F25D 25/04* (2006.01)
*F25D 25/00* (2006.01)

(52) U.S. Cl. .......................................... 62/380; 62/378
(58) Field of Classification Search .................. 62/378, 62/381
See application file for complete search history.

(56) References Cited

U.S. PATENT DOCUMENTS

| | | | | |
|---|---|---|---|---|
| 2,101,758 A | * | 12/1937 | Shaffer | 292/144 |
| 3,088,787 A | * | 5/1963 | Perkins | 312/400 |
| 3,163,994 A | * | 1/1965 | Haumann et al. | 62/218 |
| 5,205,128 A | * | 4/1993 | Richard | 62/63 |
| 5,233,844 A | * | 8/1993 | Knippscheer et al. | 62/440 |
| 5,632,388 A | * | 5/1997 | Morrison et al. | 211/74 |
| 5,733,261 A | * | 3/1998 | Obong | 604/110 |
| 5,964,095 A | * | 10/1999 | Coelho et al. | 62/62 |
| 6,167,710 B1 | * | 1/2001 | Cosman | 62/78 |
| 6,302,327 B1 | * | 10/2001 | Coelho et al. | 235/383 |
| 6,608,883 B2 | * | 8/2003 | Olson et al. | 378/79 |
| 6,918,698 B2 | * | 7/2005 | Nordmeyer et al. | 378/205 |
| 2006/0000296 A1 | * | 1/2006 | Salter | 73/863.01 |

* cited by examiner

*Primary Examiner*—William C Doerrler
(74) *Attorney, Agent, or Firm*—Gifford, Krass, Sprinkle, Anderson & Citkowski, P.C.

(57) ABSTRACT

A cryogenic storage container having a tank with an interior and an open top. At least two and preferably three trays are independently rotatably mounted within the interior of the housing so that an upper tray is positioned above one or more lower trays. Each tray has a plurality of compartments and each compartment is adapted to receive a source unit container. At least one cold working area is formed on the upper tray while an extraction tool selectively engages and moves stored unit containers from any of the trays and to the cold working area.

4 Claims, 4 Drawing Sheets

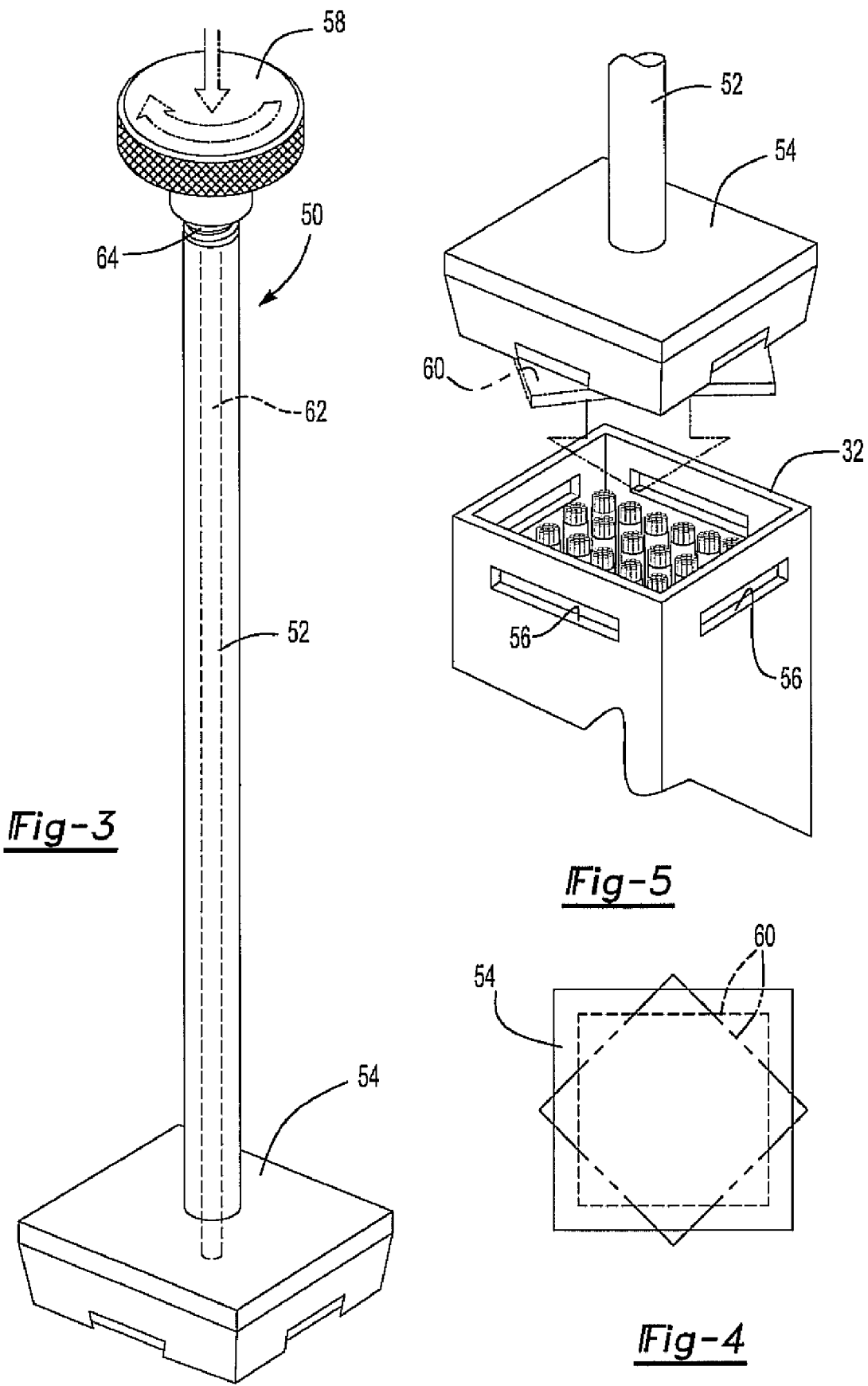

CRYOGENIC STORAGE CONTAINER SYSTEM

BACKGROUND OF THE INVENTION

I. Field of the Invention

The present invention relates to a cryogenic storage container system.

II. Description of Related Art

There are many previously known cryogenic storage container systems for storing biological specimens, e.g. sperm, blood, embryos, etc., at low temperatures, e.g. −190° C. Many of these previously known cryogenic storage containers include a cylindrical tank defining an interior in which the specimens are contained. The tank is then cooled with liquid nitrogen in order to maintain the cryogenic temperatures within the interior of the tank.

The biological specimens are typically contained within small straws which, in turn, are positioned within a storage unit container (SUC). These SUCs are typically rectangular in cross-sectional shape and dimensioned and sized to hold a plurality of biological specimens.

In order to maximize the number of biological specimens that may be contained within a single cryogenic tank, many previously known cryogenic storage containers have included a plurality of turntables which are independently rotatably mounted to each other and positioned within the interior of the tank so that the turntables are positioned one on top of each other. Each turntable, except the lowermost turntable, includes a cutout or removed section to provide access to the turntables beneath that turntable layer.

Each turntable, furthermore, includes a plurality of compartments wherein each compartment is dimensioned to receive one SUC. Consequently, by rotating the turntables relative to each other, access to any particular compartment, and thus any desired biological specimen within the interior of the cryogenic tank, may be achieved.

One previously known disadvantage of these previously known cryogenic tanks, however, is that in order to retrieve a particular SUC containing a desired biological specimen or specimens, it was necessary to move the SUC into a position above the uppermost turntable and thus, into the relative warm zone of the cryogenic tank. In some cases, this movement of the SUC caused a thawing and thus destruction of the biological specimen.

A still further disadvantage of these previously known cryogenic storage containers is that, in order to obtain and SUC from one of the lower turntables, it was necessary to snag the SUC using a hook or similar device. Such hooks, however, are time consuming and difficult to use. Furthermore, in the event that the SUC is not firmly engaged by the hook, the SUC can disengage from the hook and be damaged.

SUMMARY OF THE INVENTION

The present invention provides a cryogenic storage container system which overcomes all of the above-mentioned disadvantages of the previously known devices.

In brief, the cryogenic storage container system of the present invention comprises a cryogenic tank having an interior and an open top. An upper tray and at least one, but preferably two or more, lower trays are independently rotatably mounted to each other and positioned in the interior of the tank so that the trays are positioned one on top of each other.

Each tray includes a plurality of compartments. Each compartment, furthermore, is dimensioned to receive a standard unit container (SUC).

At least one cold working area is preferably formed on the upper tray so that SUCs selected from one of the lower turntables may be moved directly into the cold working area on the upper turntable. By doing so, the selected SUC is maintained within the cold working area of the cryogenic tank at all times, thereby protecting the biological specimens against undesired thawing.

The present invention further provides an improved extraction tool for engaging and moving selected SUCs. In the preferred embodiment of the invention, the extraction tool comprises an elongated rod having a base attached to one end. This base is dimensioned to partially fit within the open top of a selected SUC.

A latch is moveably mounted to the base and moveable between a first position in which the latch is unlocked from the SUC, and the second position, in which the latch engages the SUC and locks the SUC to the base. An actuator knob at the opposite end of the extraction tool rod is used to move the latch between its first and second position.

Preferably the SUCs include at least two, and preferably four, opposed slots adjacent an upper end of the SUC. The latch then comprises a rectangular plate rotatably mounted to the base so that, with the base position in the upper end of a selected SUC, rotation of the latch causes the latch corners to enter into the slots, thus looking the selected SUC to the base. Thereafter, the selected SUC is manipulated by the technician as desired.

BRIEF DESCRIPTION OF THE DRAWINGS

A better understanding of the present invention will be had upon reference to the following detailed description when read in conjunction with the accompanying drawings, wherein like reference characters refer to like parts throughout the several views, and in which:

FIG. 3 is an elevational view illustrating a preferred embodiment of an SUC extraction tool;

FIG. 4 is a bottom view of the extraction tool;

FIG. 5 is a fragmentary elevational view illustrating the extraction tool; and

DETAILED DESCRIPTION OF THE PREFERRED EMBODIMENTS

Figure 1:
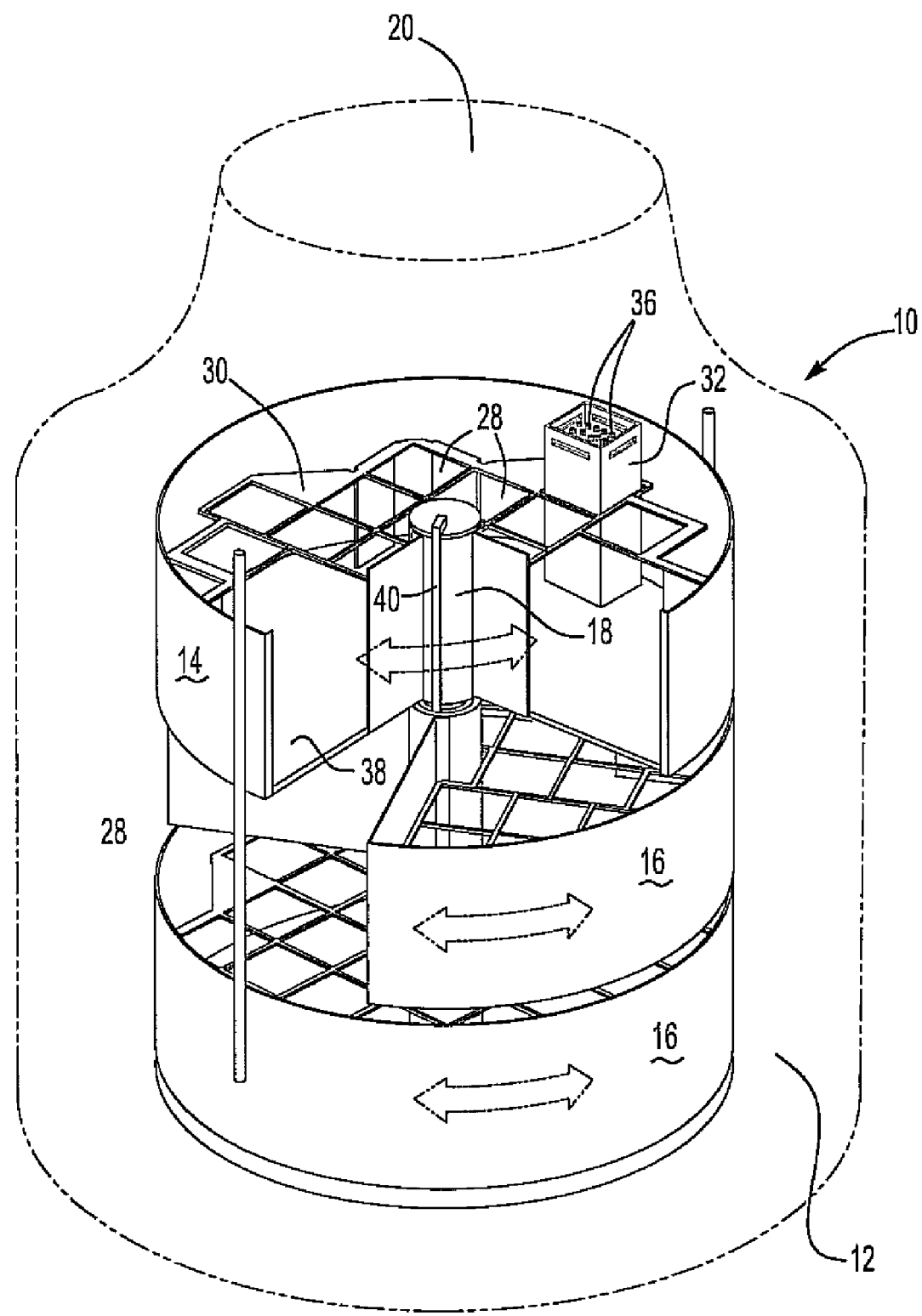
FIG. 1 is a fragmentary elevational view illustrating a preferred embodiment of the present invention.
Figure 2:
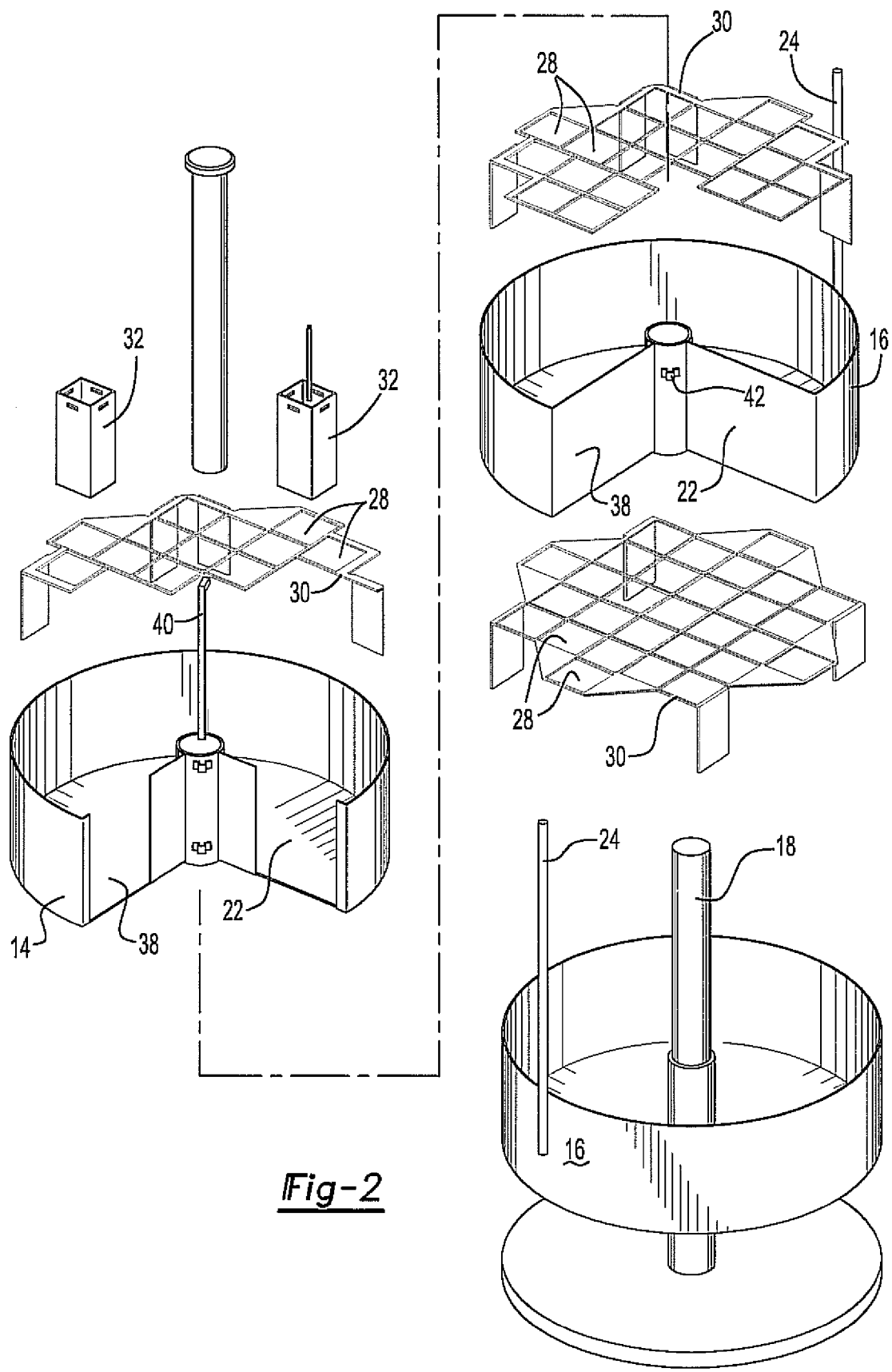
FIG. 2 is an exploded view illustrating a portion of the preferred embodiment of the present invention.

With reference first to FIGS. 1 and 2, a cryogenic storage tank 10 is shown defining an interior 12 adapted to contain biological specimens. Any conventional means (not shown) such as liquid nitrogen is utilized to maintain the interior 12 of the tank 10 at cryogenic temperatures.

An upper turntable 14 and at least one, but preferably two or more lower turntables 16 are each independently rotatably mounted to a post 18 so that the turntables 14 and 16 are positioned one on top of each other with the upper turntable 14 positioned adjacent an open top 20 of the tank 10 and the lower turntables of 16 positioned beneath the upper turntable 14.

As best shown in FIG. 2, both the upper turntable 14 and all of the lower turntables 16, except for the lowermost turntables 16, include a removed section 22. This removed section 22 thus provides access to the lower turntables 16. Furthermore, an upwardly extending handle 24 is attached to each lower turntable 16 so that an upper end of each handle 24 is positioned adjacent the open top 20 of the tank 10. Consequently, the handles 24 are used to rotate the lower turntables 16 to provide access to the desired position on any particular lower turntable 16.

With reference now to FIGS. 1 and 2, each turntable 14 and 16 is divided into a plurality of rectangular compartments 28 by a grid 30 (FIG. 2) positioned within each turntable 14 or 16. Each compartment 28, furthermore, is dimensioned to receive a storage unit container 32 (FIG. 1) designed to contain biological specimens 36. Such biological specimens 36 are typically contained in individual straws.

At least one, and preferably two cold working areas 38 are provided in the upper turntable 14. These cold working areas 38 thus allow SUCs 32 from one of the lower levels 16 to be moved directly into the cold working area 38 without exposing the selected SUC 32 to the warmer temperatures near the open top 20 of the open tank 10. Each cold working area 38, furthermore, is dimensioned to receive and support at least one SUC 32.

A mechanical slide 40 is slidably mounted to the upper turntable 14 and movable between an upper and a lower position. When in its lower position, the slide 40 engages a keeper 42 on the next lower turntable 16 in order to lock the turntables 14 and 16 together against rotation.

With reference now to FIGS. 3-5, an extraction tool 50 is provided which engages a selected SUC 32 in one of the turntables 14 or 16. The extraction tool 50 includes an elongated tube 52 having a base 54 secured to one end. This base 54 is dimensioned to fit partially within an open top of the SUC 32.

A rectangular latch 60 is mounted to the base 54 and movable between a locked position shown in phantom line in FIG. 4 and an unlocked position shown in solid line in FIG. 4. A rod 62 extends through the tube 52 and has one end secured to the latch 60. An actuator knob 58 is secured to the other end of the rod 62 for moving the latch 60 between its locked and unlocked position. A compressor spring 64 urges the latch 60 against the base 54 and holds the latch 60 in its locked or unlocked position.

As best shown in FIG. 5, the SUC 32 includes opposing slots 56 on at least two, and preferably all four of its sides. When the base 54 of the extraction tool 50 is positioned within the open top of the SUC 32, the latch 60 mounted to the base 54 of the extraction tool 50 is aligned with the slots 56.

As best shown in FIG. 4, with the base 54 of the extraction tool positioned on the selected SUC and the latch 60 moved to its unlocked position, the latch 60 is retracted from the slots 56. Conversely, when rotated to its locked position, the corners of the latch 60 protrude through the slots 56 in the SUC, thus detachably locking the SUC to the base 54 of the extraction tool 50. Thereafter, the SUV 32 may be manipulated, as desired. Once positioned in a final position, rotation of the latch 60 to its unlocked position again enables the extraction tool 50 to be detached from the SUC 32.

Figure 6A:
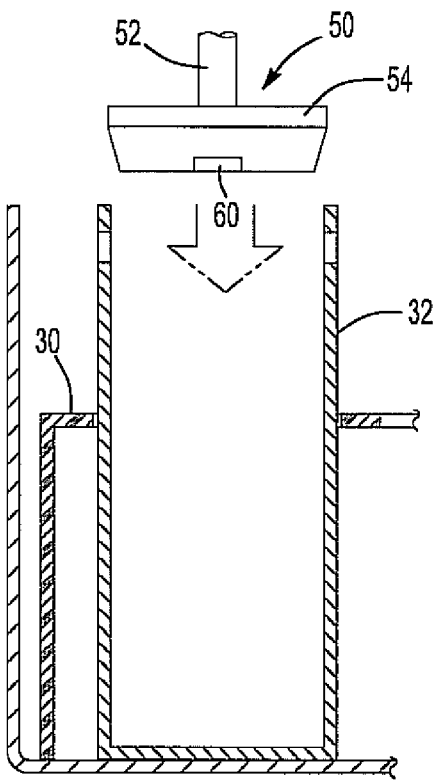
FIGS. 6A-6D are diagrammatic sectional views illustrating the operation of the extraction tool of the present invention.
Figure 6B:
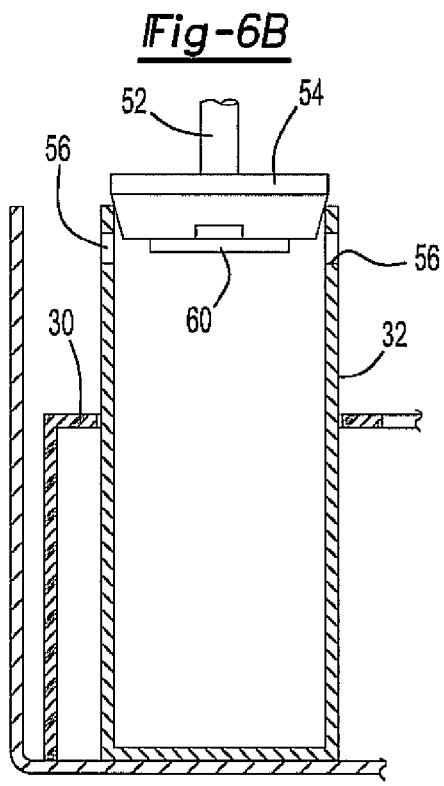

With reference now to FIGS. 6A-6D, an exemplary engagement of the extraction tool 50 with a selected SUC 32 is illustrated. In FIG. 6A, the base 54 of the extraction tool 50 is aligned with the open top of the SUC 32. The base 54 is moved to the position illustrated in FIG. 6B in which the base 54 is partially positioned within the SUC 32. In this position, the latch 60 is aligned with the slots 56 in the SUC 32.

Figure 6C:
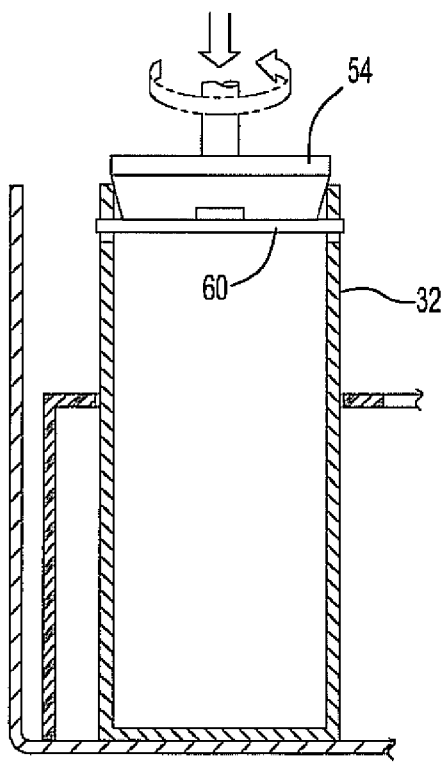
Figure 6D:
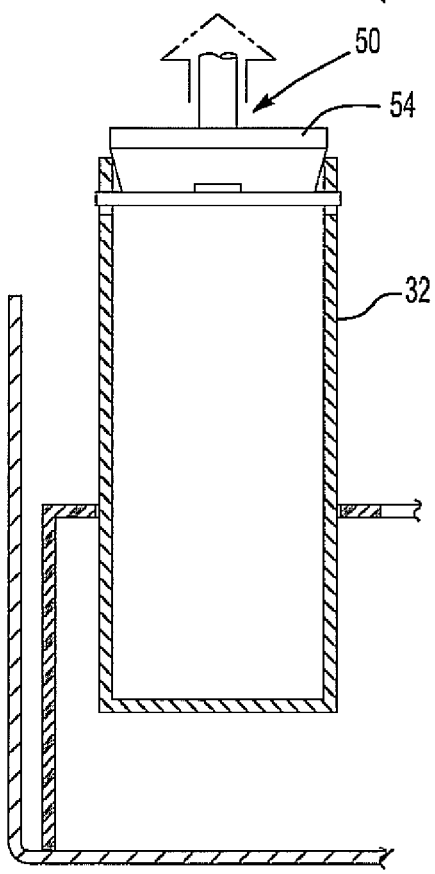

Thereafter, the latch 60 is rotated to a locked position shown in FIG. 6C in which the corners of the latch 60 extend through the SUC slots 56. At this time, the pressure of the compression spring 64 compresses the top of the SUC 32 between the extraction tool base 54 and the latch 60. In doing so, a firm engagement between the extraction tool 50 and the SUC 32 is obtained.

Thereafter, the extraction tool 50 may be used to manipulate the SUC 32 and move the SUC 32 to a desired position. After the SUC 32 is positioned as desired, the actuator 58 is utilized to rotate the latch 62 to its unlocked position, thus detaching the extraction tool 50 from the SUC 32.

From the foregoing, it can be seen that the present invention provides a simple and yet effective cryogenic storage container system for biological specimens. Having described our invention, however, many modifications thereto will become apparent to those of skill in the art to which it pertains without deviation from the spirit of the invention as defined by the scope of the appended claims.

We claim:

1. A cryogenic storage system comprising:
a tank having an interior and an open top,
an upper turntable and a lower turntable independently rotatably mounted in said interior of said tank with said upper turntable being positioned above said lower turntable,
a plurality of storage unit containers, each storage unit container being square in cross-section and having an open top and an elongated slot along each side of said storage unit container such that each slot extends parallel to a top edge of said storage unit container, each turntable having a plurality of compartments, each compartment adapted to receive one storage unit container,
a storage unit container extraction tool for selectively engaging and moving one storage unit container, said extraction tool comprising an elongated rod, a base mounted to one end of said rod and dimensioned to engage said open top, a latch mounted to said base and rotatable between an unlocked position in which said base and a selected storage unit container are separable from each other, and a locked position in which portions of said latch extend through at least two of said slots in said selected storage unit container and secures said selected storage unit container to said base by sandwiching a portion of the selected storage unit container between the base and the latch portions.

2. The invention as defined in claim 1 and comprising an actuator mounted to the other end of said rod for moving said latch between said locked and said unlocked position.

3. The invention as defined in claim 1 wherein said latch portions extend through all four of said slots when said latch is in said locked position.

4. The invention as defined in claim 2 and comprising a spring which resiliently locks said latch in one of said locked or unlocked position.

* * * * *